(12) United States Patent
Fujimoto et al.

(10) Patent No.: US 10,595,115 B2
(45) Date of Patent: Mar. 17, 2020

(54) EARPHONE

(71) Applicant: Panasonic Intellectual Property Management Co., Ltd., Osaka (JP)

(72) Inventors: Keisuke Fujimoto, Osaka (JP); Yushi Ogino, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/414,211

(22) Filed: May 16, 2019

(65) Prior Publication Data

US 2019/0281378 A1 Sep. 12, 2019

Related U.S. Application Data

(63) Continuation of application No. 15/879,977, filed on Jan. 25, 2018, now Pat. No. 10,341,757, which is a continuation of application No. PCT/JP2016/003554, filed on Aug. 2, 2016.

(30) Foreign Application Priority Data

Aug. 5, 2015 (JP) .................................. 2015-155497

(51) Int. Cl.
*G01J 1/44* (2006.01)
*H04R 3/00* (2006.01)
(Continued)

(52) U.S. Cl.
CPC ......... *H04R 1/1041* (2013.01); *A61B 5/0084* (2013.01); *A61B 5/1123* (2013.01);
(Continued)

(58) Field of Classification Search
CPC ... A61B 5/0084; A61B 5/1123; A61B 5/1128; A61B 5/6817; A61B 5/7475;
(Continued)

(56) References Cited

U.S. PATENT DOCUMENTS

| 9,609,420 B2 | 3/2017 | Azmi |
| 2010/0069705 A1 | 3/2010 | Schumaier |

(Continued)

FOREIGN PATENT DOCUMENTS

| JP | 2012-518515 | 8/2012 |
| WO | 2010/090175 | 8/2010 |
| WO | 2010/098912 | 9/2010 |

OTHER PUBLICATIONS

International Search Report of PCT application No. PCT/JP2016/003554 dated Oct. 25, 2016.

*Primary Examiner* — Paul Kim
*Assistant Examiner* — Friedrich Fahnert
(74) *Attorney, Agent, or Firm* — Wenderoth, Lind & Ponack, L.L.P.

(57) ABSTRACT

An earphone includes an audio transmitter, a housing, a sound passage pipe, a radiator, and a light receiver. The audio transmitter transmits sound. The housing has an internal space for containing the audio transmitter. The sound passage pipe guides sound produced at the audio transmitter into an external auditory canal. The radiator radiates light into the external auditory canal. The light receiver is disposed in the internal space of the housing. The light receiver converts the light into a signal, the light having been reflected off the external auditory canal and passed through an internal space of the sound passage pipe. The housing, the sound passage pipe, and the radiator are disposed in this order.

3 Claims, 8 Drawing Sheets

(51) Int. Cl.
    *H04R 1/10*      (2006.01)
    *A61B 5/00*      (2006.01)
    *A61B 5/11*      (2006.01)
    *G01J 1/02*      (2006.01)
    *H04R 1/28*      (2006.01)

(52) U.S. Cl.
    CPC .......... *A61B 5/1128* (2013.01); *A61B 5/6817* (2013.01); *A61B 5/7475* (2013.01); *G01J 1/0271* (2013.01); *G01J 1/44* (2013.01); *H04R 1/1016* (2013.01); *H04R 1/2857* (2013.01); *H04R 1/2811* (2013.01); *H04R 3/00* (2013.01); *H04R 2420/07* (2013.01); *H04R 2460/03* (2013.01); *H04R 2460/15* (2013.01)

(58) Field of Classification Search
    CPC ........ G01J 1/0271; G01J 1/44; H04R 1/1016; H04R 1/1041; H04R 1/2811; H04R 1/2857; H04R 2420/07; H04R 2460/03; H04R 2460/15; H04R 3/00
    USPC ...... 381/74, 312, 322, 328, 380, 384; 345/7, 345/8, 9, 156, 157, 158, 207; 600/25
    See application file for complete search history.

(56)         References Cited

U.S. PATENT DOCUMENTS

| | | |
|---|---|---|
| 2011/0038503 A1 | 2/2011 | Yang |
| 2012/0001846 A1 | 1/2012 | Taniguchi et al. |
| 2015/0109773 A1 | 4/2015 | Li |
| 2016/0013239 A1 | 1/2016 | Kasaoka |
| 2016/0277837 A1 | 9/2016 | Sato |
| 2017/0040496 A1 | 2/2017 | Martin |
| 2017/0219786 A1 | 8/2017 | Morioka |

EARPHONE

BACKGROUND

1. Technical Field

The present disclosure relates to an earphone capable of sending signals for controlling an external device.

2. Description of the Related Art

Technologies that have been presented in recent years to fulfill hands-free operation and other purposes enable the transmission of signals for controlling an external device from an earphone put on an ear without using hand.

For example, PCT Japanese Translation Patent Publication No. 2012-518515 discloses an earphone that includes a speaker, a photoemitter, and a photodetector. The earphone transmits sound from the speaker and collects physiological information from an ear by emitting light from the photoemitter and letting the photodetector detect the light reflected off an inside of the ear.

WO 2010/090175 discloses an earphone that includes an optical sensor for detecting a change in the shape of an external auditory canal as a change in distance. The earphone allows the optical sensor to send a signal that changes in line with an intentional change in the shape of the external auditory canal and controls an external device in response to a change in the signal sent from the optical sensor.

A conventional earphone that controls an external device in line with an intentional change in a state of an external auditory canal has a passage for sound transmitted from a speaker and a passage for light leaving a light emitter and entering a light receiver. The two passages are separated from each other. If the passage for sound gets widened to improve sound quality, the passage for light gets narrow. This causes the quantity of light reaching the light receiver to decrease and makes it difficult to detect a change in the state of the external auditory canal. Presumably, both the passages for sound and light can be widened to achieve both the improvement of sound quality and the maintenance of detection sensitivity. Unfortunately, widening the passages to a certain degree or greater is impossible because of a size restriction on a section of the external auditory canal through which the earphone is inserted.

Disposing the light emitter and the light receiver on the sound passage to optically detect the state of the external auditory canal increases the quantity of light reaching the light receiver. Unfortunately, the light emitter and the light receiver constitute an obstacle to sound propagation and hamper the earphone from fulfilling its original function, i.e. production of sound having good sound quality.

SUMMARY OF THE INVENTION

The present disclosure provides an earphone that can accurately convert a change in a state of an external auditory canal into a signal while ensuring sound quality required for the earphone.

An earphone according to an aspect of the present disclosure includes an audio transmitter configured to transmit sound, a housing having an internal space for containing the audio transmitter, a sound passage pipe having a tubular shape and configured to be inserted into an external auditory canal to guide sound produced at the audio transmitter into the external auditory canal, a radiator configured to radiate light into the external auditory canal, and a light receiver disposed in the internal space of the housing and configured to convert the light into a signal, the light having been reflected off the external auditory canal and passed through an internal space of the sound passage pipe. The housing, the sound passage pipe, and the radiator are disposed in this order.

The earphone according to the aspect of the present disclosure can accurately convert a change in a state of the external auditory canal into a signal while ensuring sound quality required for the earphone.

DETAILED DESCRIPTION OF THE INVENTION

The present disclosure, accomplished to offset these disadvantages, aims to provide an earphone that can convert a change in a state of an external auditory canal into a signal with improved accuracy while ensuring sound quality required for the earphone.

Hereinafter, exemplary embodiments will be described in detail with reference to the drawings as appropriate. However, in some cases, detailed description more than necessary may be omitted. For example, detailed description of well-known matters or repeated description of substantially the same configuration may be omitted. This is to avoid the following description from being unnecessarily redundant, and to facilitate understanding of those skilled in the art.

The inventor of the present disclosure provides the appended drawings and the following description in order to allow those skilled in the art to fully understand the present disclosure, and does not intend to limit the subject matter described in the appended claims by the appended drawings and the following description.

Exemplary Embodiments

Figure 1:
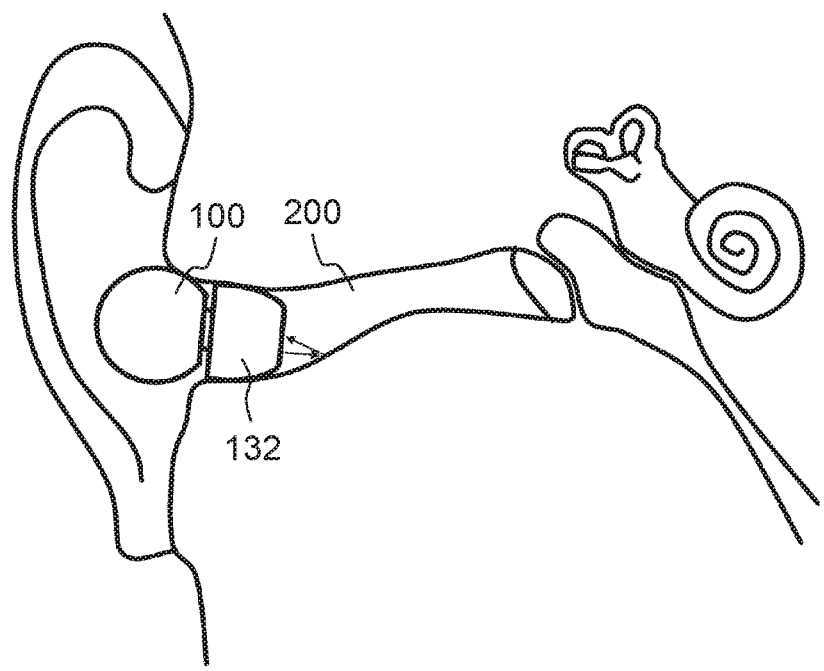
FIG. 1 is a schematic view of an earphone put on an ear.

FIG. 1 is a schematic view of an earphone put on an ear.

With reference to FIG. 1, earphone 100 is a device designed to be put on an ear and transmit sound that is converted from audio signals sent from an external device (not shown) such as a music player or a smartphone. Earphone 100 is held in place by having ear pad 132 inserted into external auditory canal 200.

Figure 2:
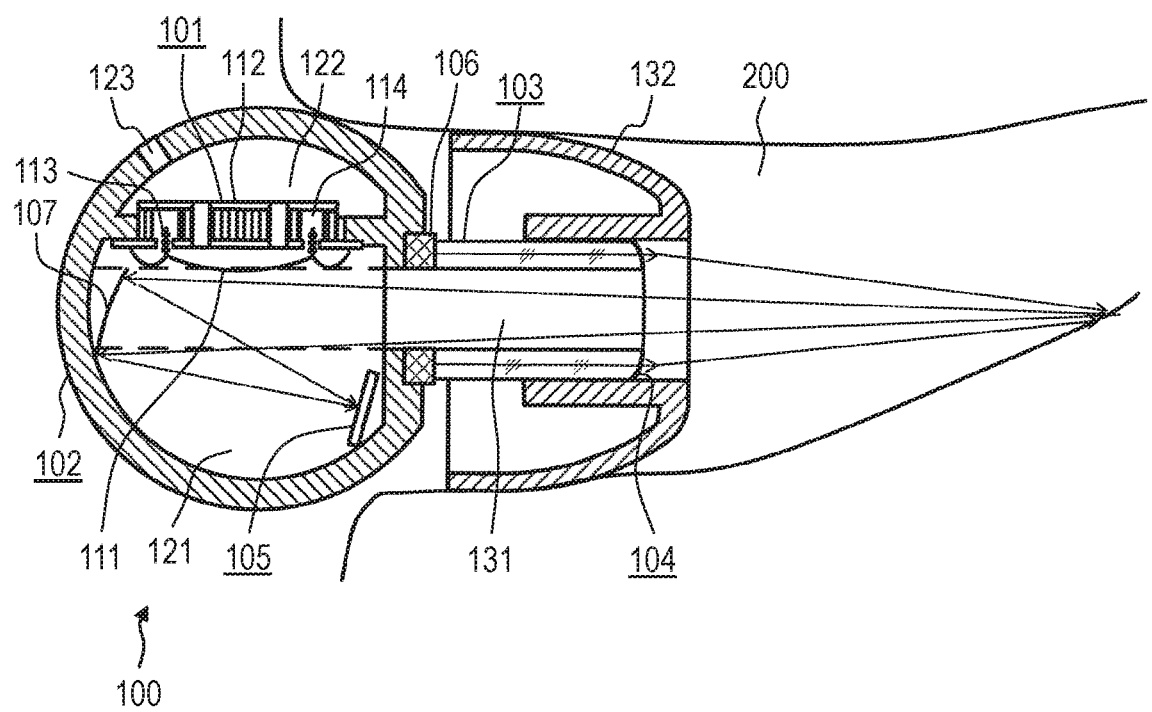
FIG. 2 is a cross-sectional view of the earphone put on an ear.

FIG. 2 is a cross-sectional view of the earphone put on an ear.

With reference to FIG. 2, earphone 100 includes audio transmitter 101, housing 102, sound passage pipe 103, radiator 104, and light receiver 105. In this exemplary embodiment, earphone 100 is equipped with light emitter 106 and reflector 107.

Audio transmitter 101 is a component known as a speaker, a driver unit, or the like and is designed to transmit sound converted from audio signals. Audio transmitter 101 includes diaphragm 111 to emit sound by vibration and magnetic circuit 112 to let diaphragm 111 vibrate. Magnetic circuit 112 is fixed to housing 102 so as to form magnetic gap 114. Voice coil 113 is attached to diaphragm 111 such that voice coil 113 is inserted in magnetic gap 114. Audio transmitter 101 is a dynamic driver unit that transmits sound by letting diaphragm 111 vibrate based on audio signals fed to voice coil 113.

Audio transmitter 101 may be any type of driver unit other than the dynamic type, with the proviso that the driver unit is built on a principle that sound is emitted by driving diaphragm 111.

Housing 102 is a component shaped like a case in external appearance. Housing 102 has a spherical (including substantially spherical) internal space for containing audio transmitter 101. The internal space of housing 102 is divided into first chamber 121 and second chamber 122 by audio transmitter 101 mounted in the internal space.

First chamber 121 is a room communicating with sound passage 131, i.e. an internal space of sound passage pipe 103 mounted on housing 102. In this exemplary embodiment, diaphragm 111 of audio transmitter 101 is disposed in first chamber 121. This configuration enables sound emitted from diaphragm 111 by vibration to bypass obstacles such as magnetic circuit 112 and directly propagate through sound passage 131 into external auditory canal 200.

Housing 102 is provided with communicating hole 123 that allows second chamber 122 to communicate with the outside and thereby dampens pressure change in second chamber 122 due to vibration of diaphragm 111. Housing 102 is formed from a light-shielding material such that light is allowed to directly enter first chamber 121 only through sound passage 131.

Preferably, an inner surface of housing 102 should be made up of an optical absorbent to prevent light (stray light) other than light reflected off reflector 107 from being incident on light receiver 105.

Audio transmitter 101 is disposed in a region other than a region that is defined by extending sound passage 131, which is the internal space of sound passage pipe 103, straight (a region enclosed by dashed lines in FIG. 2). This configuration enables light (light reflected off external auditory canal 200) to be incident on light receiver 105 via sound passage 131 without being disturbed by audio transmitter 101.

Sound passage pipe 103 is an acoustic tube made up of a tubular component having openings at both ends. Sound passage pipe 103 guides sound produced at audio transmitter 101 into external auditory canal 200. One end (top end) of sound passage pipe 103 is put in a neighborhood of an opening of external auditory canal 200, whereas the other end (bottom end) of sound passage pipe 103 is connected with housing 102. Sound passage 131 of sound passage pipe 103 communicates with first chamber 121, i.e. a part of the internal space of housing 102.

A vertical cross section of the internal space of housing 102 is larger than a vertical cross section of the internal space of sound passage pipe 103. The vertical cross sections herein are cross sections perpendicular to a lengthwise axis of tubular sound passage pipe 103. The sizes of their vertical cross sections are compared by taking largest areas of the vertical cross sections of the respective internal spaces. A capacity of housing 102 is larger than a capacity of sound passage pipe 103. This configuration ensures that sound emitted from diaphragm 111 by vibration in housing 102 does not directly propagate into sound passage pipe 103 having high acoustic resistance and thus prevents sound quality from lowering.

Sound passage pipe 103 is a transparent component designed to guide light emitted from light emitter 106, which is disposed on the bottom end of sound passage pipe 103 adjacent to housing 102, and radiate the guided light from the top end of sound passage pipe 103. The top end of sound passage pipe 103 serves as radiator 104. Housing 102, sound passage pipe 103, and radiator 104 are disposed in this order, with the radiator 104 clearly outside the housing 102 as shown in FIG. 2. An inner peripheral surface of sound passage pipe 103 is provided with a shielding film or a reflective film (not shown) to prevent guided light from leaking to sound passage 131. This configuration prevents light from leaking out of sound passage pipe 103, reaching light receiver 105, and being superimposed as noise on signals.

The top end of sound passage pipe 103 serving as radiator 104 has a curved lens surface designed to concentrate radiated light on an inner peripheral surface of external auditory canal 200. This configuration enables radiated light to concentrate on one place in external auditory canal 200 and thus produces strong reflected light. This in turn enables the earphone to accurately grasp a change in a state of external auditory canal 200.

In this exemplary embodiment, sound passage pipe 103 is held in place with ear pad 132 inserted into external auditory canal 200. Ear pad 132 is a flexible component that is detachably attached to an outer peripheral surface of sound passage pipe 103 and put around the surface. Ear pad 132 changes in shape so as to be suited to a shape of external auditory canal 200 into which the ear pad is inserted.

Since sound passage pipe 103 is held in place with ear pad 132 inserted into external auditory canal 200 as described above, size of sound passage 131, which is a passage for sound, is limited to size of external auditory canal 200 of the generic person. Thus, sound passage pipe 103 is smaller than an earhole of the generic person.

Light receiver 105 is a photoelectric transducer disposed in the internal space of housing 102 and is designed to convert the light into a signal, the light having been reflected off external auditory canal 200 and passed through sound passage 131 of sound passage pipe 103. Light receiver 105 is any transducer that can convert the light into electric signals. For example, light receiver 105 may be a transducer that converts a quantity of received light into an electric signal or a converter that has a plurality of arranged photoelectric transducers and converts light quantities at the respective transducers into signals. Light receiver 105 may be a transducer that converts colors into signals. Specifically, examples of light receiver 105 include photoconductive cells, phototransistors, photovoltaic cells, and other photoelectric transducers called photocells. Alternatively, light receiver 105 may be an image sensor such as a charge-coupled device (CCD) or a complementary metal oxide semiconductor (CMOS).

In this exemplary embodiment, light receiver 105 is disposed in a room where diaphragm 111 of audio transmitter 101 is disposed, that is in first chamber 121 of housing 102. Light receiver 105 is disposed in a region other than a region exposed directly to sound transmitted from audio transmitter 101, that is the region defined by extending sound passage 131, which is the internal space of sound passage pipe 103, (the region enclosed by dashed lines in FIG. 2).

This configuration prevents light receiver 105 from having an influence on the transmission of sound transmitted from audio transmitter 101 and thus ensures sound quality required for earphone 100.

Reflector 107 is a component used to reflect reflected light that has passed through sound passage 131 onto light receiver 105. Reflector 107 is disposed in the internal space of housing 102. In this exemplary embodiment, reflector 107 is disposed in the region defined by extending sound passage 131 of sound passage pipe 103 straight (the region enclosed by dashed lines in FIG. 2) in first chamber 121 of housing 102.

This configuration enables the earphone to guide light that has been reflected off external auditory canal 200 and passed through sound passage 131 of sound passage pipe 103 to light receiver 105 and effectively use the space inside housing 102. Reflector 107 is disposed more distant from sound passage pipe 103 than audio transmitter 101 is. This configuration prevents reflector 107 from having an influence on the transmission of sound transmitted from audio transmitter 101 and thus ensures sound quality required for earphone 100.

No particular limitation is placed on the material and other properties of reflector 107. However, it is preferable that the material of reflector 107 reflect light that has been reflected off external auditory canal 200 and passed through sound passage 131 with high efficiency. Reflector 107 may include a concave surface designed to concentrate light that has passed through sound passage 131 onto light receiver 105. Reflector 107 may be integrated with housing 102 and have a reflective film formed on a surface of the housing to reflect light that has passed through sound passage 131, for example.

Light emitter 106 is an element that emits light. Examples of light emitter 106 include light-emitting diodes and semiconductor lasers. In this exemplary embodiment, annular-shaped light emitter 106 is mounted on the bottom end of sound passage pipe 103 and mounted into housing 102. Light emitter 106 includes a plurality of annularly-disposed inorganic light-emitting diodes that have respective optical axes extending toward the top end of sound passage pipe 103. This configuration enables the light emitter to project strong light onto external auditory canal 200 and allows an increased quantity of light to be reflected off external auditory canal 200, pass through sound passage 131, and reach the internal space of housing 102. Thus, the earphone can accurately convert a change in the state of external auditory canal 200 into a signal. In this exemplary embodiment, light emitter 106 includes the annularly-disposed inorganic light-emitting diodes. However, light emitter 106 may have any other configuration, with proviso that the configuration enables the light emitter to project strong light onto external auditory canal 200. For example, light emitter 106 may include a flexible organic light-emitting diode that is disposed along an inner or outer peripheral curved surface of the bottom end of sound passage pipe 103 and designed to emit planar light.

Earphone system 300 that includes earphone 100 described above will now be described.

Figure 3:
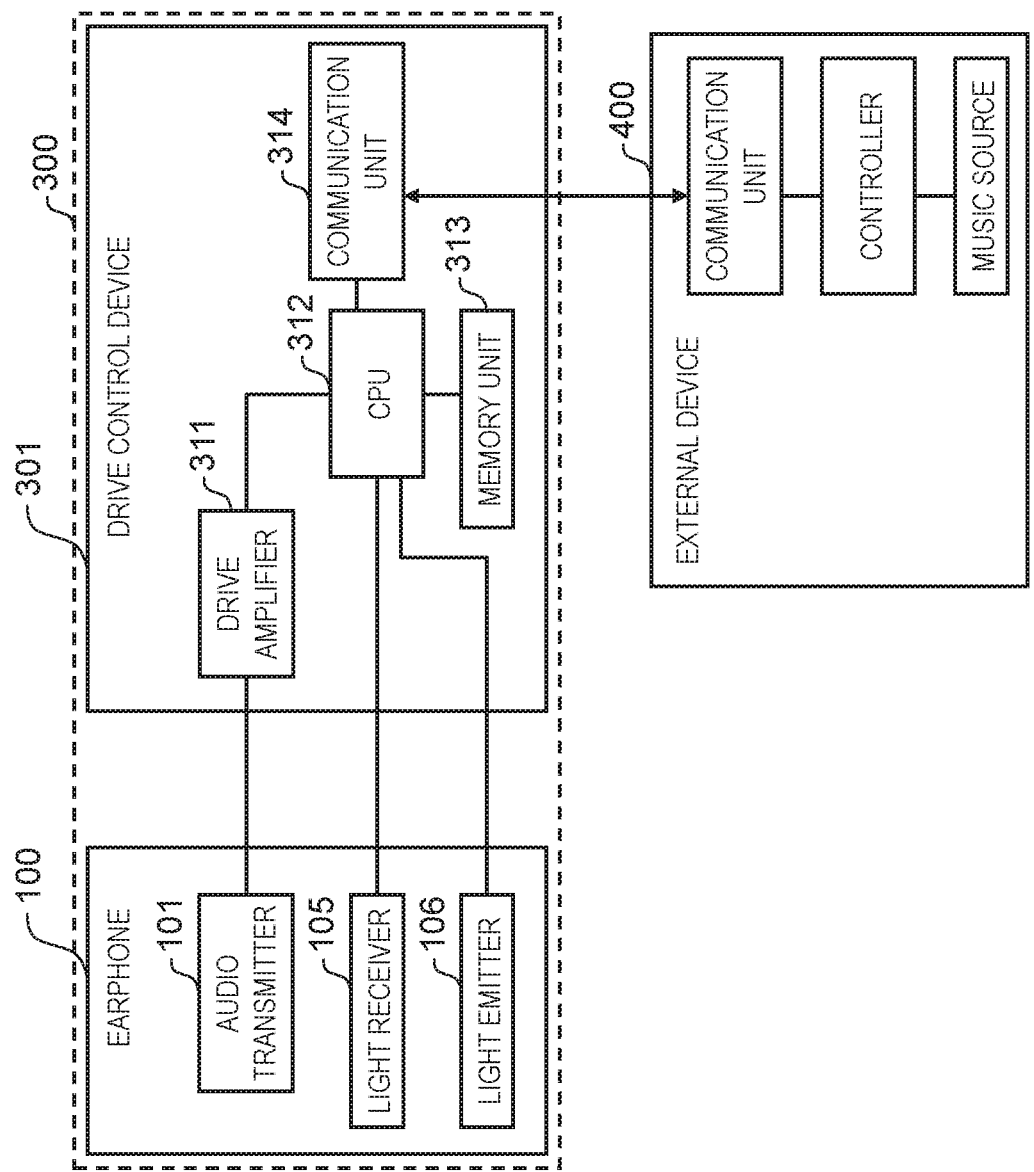
FIG. 3 is a block diagram illustrating both a configuration of an earphone system and an external device.

FIG. 3 is a block diagram illustrating both a configuration of the earphone system and an external device.

With reference to FIG. 3, earphone system 300 is a system that receives an audio signal from external device 400 for sending audio signals and transmits sound. At the same time, earphone system 300 is used to control external device 400 in response to signals sent from earphone 100, for example.

Earphone system 300 is connected with a music player acting as external device 400. Earphone system 300 includes earphone 100 and drive control device 301.

Drive control device 301 is a device used to let earphone 100 transmit sound and control external device 400 in response to signals sent from earphone 100. Drive control device 301 includes drive amplifier 311, central processing unit (CPU) 312, memory unit 313, and communication unit 314. Drive control device 301 is connected with earphone 100 by wire and is disposed in a neighborhood of the back of a neck (a nape) while earphone 100 is put on an ear. Drive control device 301 feeds signals to light emitter 106 to let light emitter 106 emit light and is equipped with a battery for driving CPU 312 and other purposes. Nothing but earphone 100 is connected with drive control device 301 by wire. Drive control device 301 wirelessly communicates with external device 400.

Drive amplifier 311 is a component used to send a signal (an analog signal) for driving audio transmitter 101 of earphone 100.

CPU 312 is a central processing unit that runs a control program and other software stored in memory unit 313 to drive light emitter 106 and generates signals for controlling external device 400 in response to signals sent from light receiver 105.

Memory unit 313 is a device that stores evaluation patterns, i.e. signal patterns used to convert signals sent from light receiver 105 into signals for controlling external device 400, and software such as a program for other processing.

Communication unit 314 is a device designed to communicate with external device 400. In this exemplary embodiment, external device 400 and drive control device 301 communicate with each other wirelessly. Specifically, examples of the wireless technology used herein include wireless communications in conformance with commonly used wireless communication standards such as Bluetooth (registered trademark), digital enhanced cordless telecommunications (DECT), or Zigbee (registered trademark). The devices may communicate with each other by wire.

A method of controlling external device 400 by using earphone system 300 will now be described.

Figure 4:
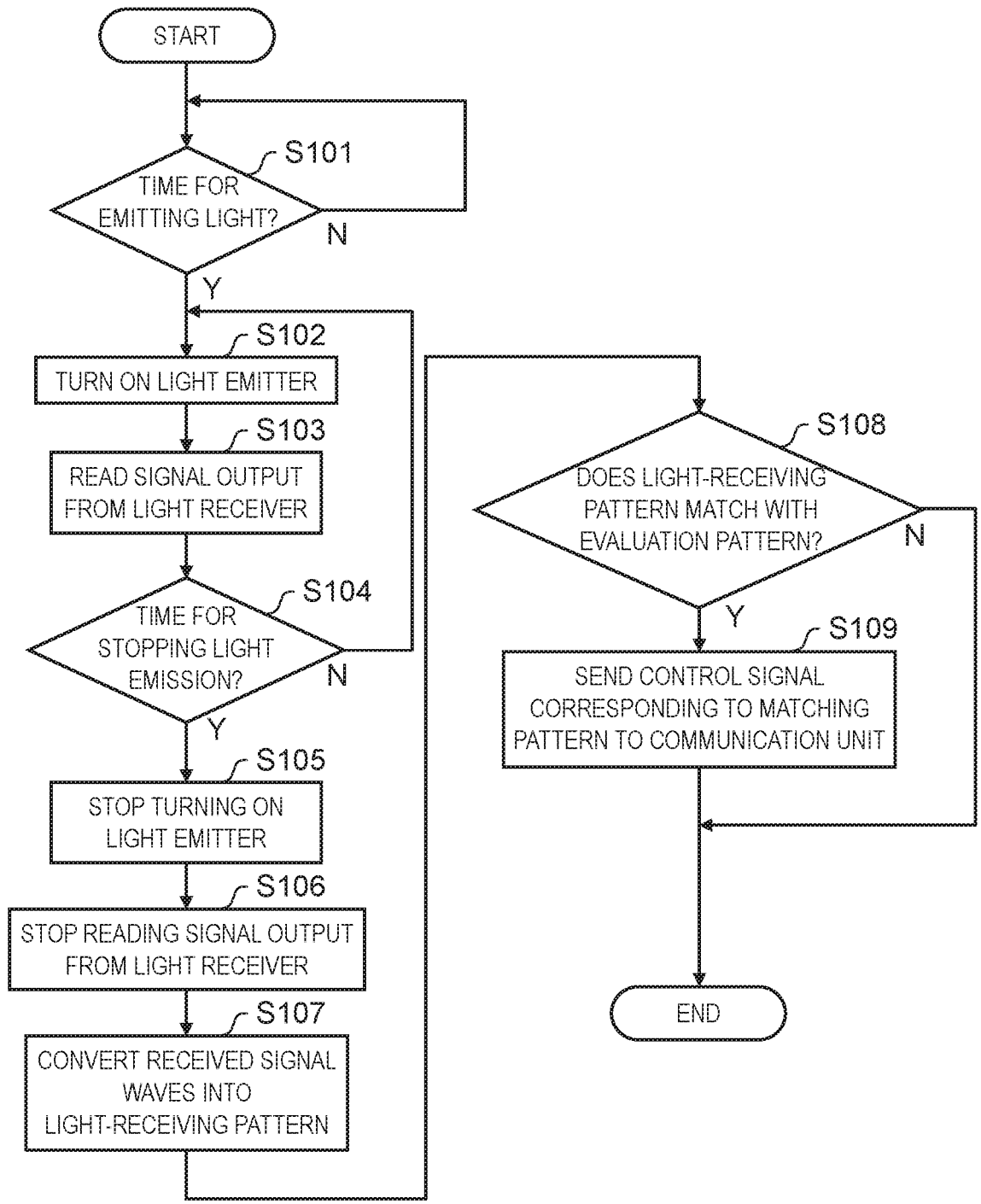
FIG. 4 is a flowchart illustrating a method of controlling an external device by using the earphone system.
Figure 5A:
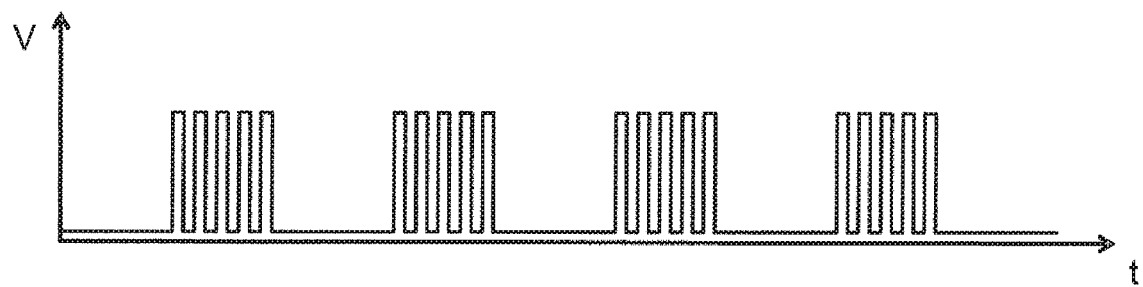
FIG. 5A is a graph illustrating a state of light emission for use in controlling the external device.
Figure 5B:
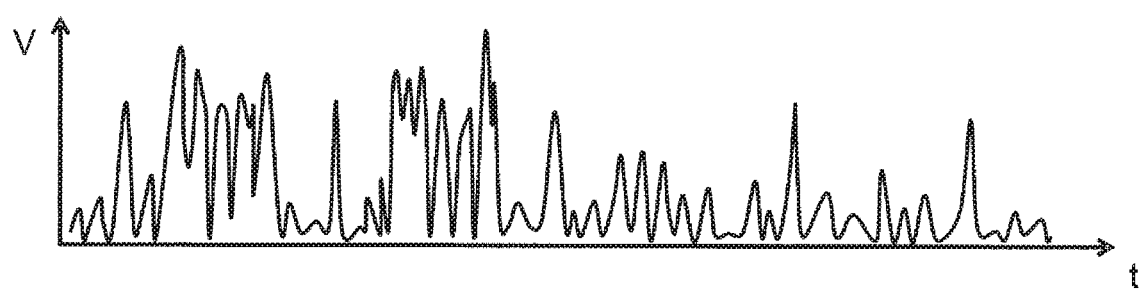
FIG. 5B is a graph illustrating a state of signal waves for use in controlling the external device.
Figure 5C:
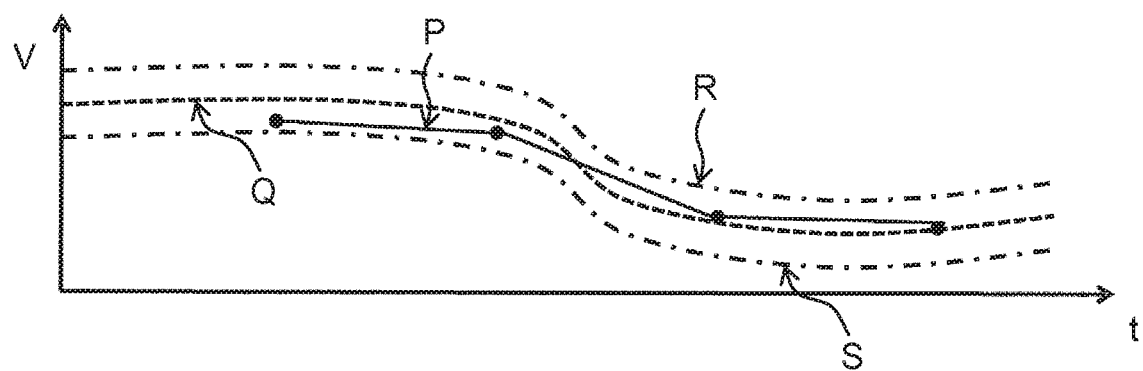
FIG. 5C is a graph illustrating a state of an external auditory canal and others for use in controlling the external device.

FIG. 4 is a flowchart illustrating the method of controlling the external device by using the earphone system. FIG. 5A is a graph illustrating a state of light emission for use in controlling the external device. FIG. 5B is a graph illustrating a state of signal waves for use in controlling the external device. FIG. 5C is a graph illustrating a state of an external auditory canal and others for use in controlling the external device.

With reference to FIG. 4, when a time for light emission comes (Y in step S101), CPU 312 turns on light emitter 106 provided on earphone 100 (step S102). CPU 312 then starts reading signal waves output from light receiver 105 (step S103). Turning on light emitter 106 (step S102) and starting reading signal waves output from light receiver 105 (step S103) may be performed in inverse order or simultaneously.

No particular limitation is placed on the pattern of light-emission signals sent by drive control device 301 for turning on light emitter 106. In this exemplary embodiment, as shown in FIG. 5A, the drive control device repeats pulsed light emission more than once and gets light emitter 106 to emit pulses of light such that a group of the pulses is formed. Taking the group of the pulses as one time span, the drive control device determines whether or not the person has intentionally changed the state of external auditory canal 200. In each of FIGS. 5A to 5C the horizontal axis shows time [t], and the vertical axis shows signal strength [V].

CPU 312 performs the turning-on of light emitter 106 (step S102) and the reading of signal waves output from light receiver 105 (step S103) as described above until a time for stopping light emission comes (N in step S104). When the time for stopping light emission comes (Y in step S104), CPU 312 stops turning on light emitter 106 (step S105) and stops reading signal waves output from light receiver 105 (step S106).

With reference to FIG. 5B, the strength of output signals of light receiver 105 read by CPU 312 is proportional to the quantity of light received by light receiver 105, for example. The signals, however, contain much noise.

CPU 312 determines a correlation between a waveform of the light emitted from light emitter 106 (FIG. 5A) and the output signals of light receiver 105 by multiplying the strengths of the respective signal waves together. Then, CPU 312 calculates an average signal strength for each of the pulse groups to remove noise and acquires light-receiving pattern P indicated with black dots and a solid line in FIG. 5C (step S107).

Noise may be removed by any method other than the process described above. For example, noise components may be removed by preparing a light-emission signal as a carrier wave of a pulse-group waveform that is modulated in any properties such as amplitude, phase, frequency, or pulse and performing demodulation corresponding to the modulation method on measured output signals of light receiver 105. Noise may be removed by applying a band-pass filter as hardware to signals output from the light receiver in order to selectively allow signals with frequencies in the neighborhood of a light-emission cycle to pass through. Alternatively, noise components may be removed through use of a digital filter in the form of software run by CPU 312 to selectively allow signals with frequencies in the neighborhood of a light-emission cycle to pass through.

Then, CPU 312 compares light-receiving pattern P acquired above with various evaluation patterns stored in memory unit 313 to detect an intentional change made in the state of external auditory canal 200 by the person (step S108).

Dashed line Q in FIG. 5C, for example, represents an evaluation pattern that is formed if the person wearing earphone 100 intentionally clenches his/her back teeth. This pattern is produced due to a decrease in the quantity of light received by light receiver 105 in response to a change in distance between a portion of external auditory canal 200 and light receiver 105 because of a change made in the form of the external auditory canal when the person wearing earphone 100 intentionally clenches his/her back teeth.

CPU 312 determines whether these patterns match or not. Specifically, CPU 312 determines whether or not light-receiving pattern P is inside a range between maximum and minimum traces indicated with dot-and-dash lines R and S in FIG. 5C, i.e. tolerance limits added to evaluation pattern Q.

If, as with light-receiving pattern P being inside the range in FIG. 5C, a matching evaluation pattern exists (Y in step S108), CPU 312 sends a control signal corresponding to the evaluation pattern to external device 400 via communication unit 314 (step S109).

CPU 312 repeats the process described above at predetermined intervals (periodically) and thus the earphone system can detect an intentional action performed by the person.

Earphone system 300 described above has no obstacle to the transmission of sound to sound passage 131 and thus allows earphone 100 to maintain quality in terms of transmitting sound that is converted from music and other audio signals sent from external device 400. Earphone system 300 can detect an intentional change in the state of external auditory canal 200 by the use of substantial quantity of light passing through sound passage 131 without obstacles to the light passage. As a result, earphone system 300 enables the person to properly control external device 400 without using hand by intentionally changing the state of external auditory canal 200.

Light emitter 106 is used to emit pulsed light and thus noise can be readily separated from signals. This configuration enables accurate detection of a change in the state of external auditory canal 200 even if the quantity of light passing through sound passage 131 is small. This configuration also enables the time for light emission to be shortened and thus reduces the consumption of electricity by the battery included in drive control device 301.

In FIGS. 5A to 5C, the signal strength is represented by voltage values. The signal strength may be represented by current values [A].

The scope of the present disclosure should not be limited to the exemplary embodiment described above. For example, another exemplary embodiment according to the present disclosure may be implemented by freely combining components described herein or excluding some of the components. The scope of the present disclosure should include any modifications obtainable through various design changes to the above exemplary embodiments that can be conceived by those skilled in the art without deviating from the spirit of the present disclosure, that is, the meaning of the wording as defined by the appended claims.

Figure 6:
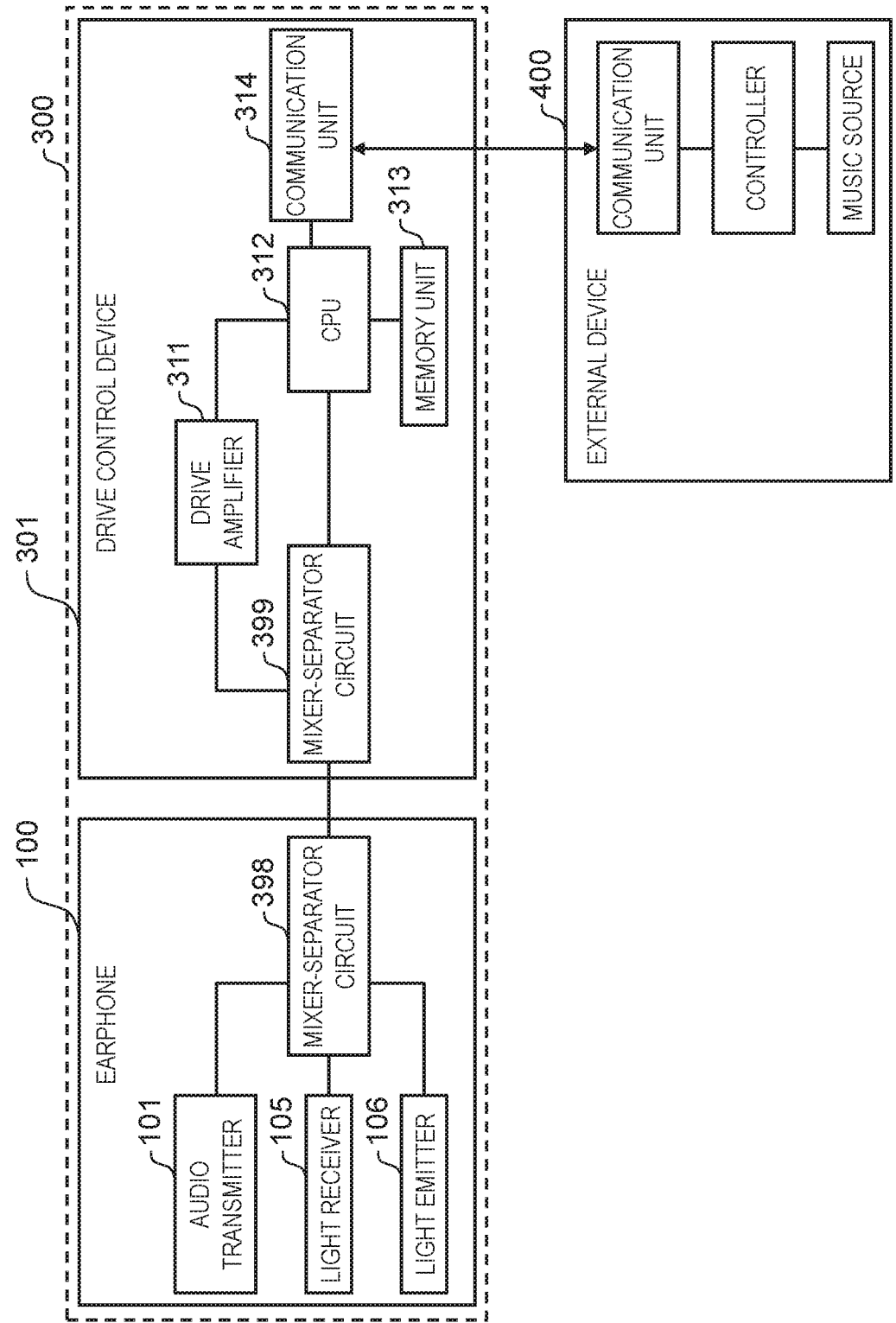
FIG. 6 is a block diagram illustrating both a configuration of an earphone system according to another exemplary embodiment and an external device.

FIG. 6 is a block diagram illustrating both a configuration of an earphone system according to another exemplary embodiment and an external device.

With reference to FIG. 6, earphone 100 and drive control device 301 may include mixer-separator circuits 398, 399 respectively, for example. Specifically, mixer-separator circuit 399 in drive control device 301 is a circuit that superimposes audio signals output from drive amplifier 311 on light-emission signals having a frequency higher than the frequency of the audio signals and outputs the superimposed signals. Mixer-separator circuit 398 in earphone 100 includes a low-pass filter and a high-pass filter. Mixer-separator circuit 398 drives audio transmitter 101 via signals that have passed through the low-pass filter and drives light emitter 106 via signals that have passed through the high-pass filter. Mixer-separator circuit 398 also has a function of sending signals output from light receiver 105 to mixer-separator circuit 399 of drive control device 301.

Mixer-separator circuits 398, 399 may each include a 2-wire to 4-wire converter for use in analog telephones and other devices. Specifically, the converter is a circuit that includes a bridge circuit, a negative impedance circuit, and a center tapped transformer and merges transmitting signals and receiving signals into a pair of signal wires to implement two-way communication.

The configuration described above decreases a number of conductors for connecting earphone 100 with drive control device 301 and allows the person to feel less awkward with wiring around his/her ear.

Change in the state of external auditory canal 200 may be detected using any method other than the method of measuring the quantity of light that has been reflected off external auditory canal 200 and passed through sound passage 131 as in the exemplary embodiment described above. For example, light receiver 105 may include a plurality of elements arranged on a two-dimensional surface and an earphone system may use a method involving taking an image of an inner surface of an external auditory canal through light receiver 105 at a predetermined light-emission time, extracting a relative position of an image pattern common to data on the images taken at different measurement times, and detecting a travel speed of the image pattern.

Light emitter 106 may follow a pattern of periodically emitting light of a single pulse other than the pattern of periodically emitting the group of pulses. Alternatively, light emitter 106 may be always left turned on.

The evaluation patterns described above are stored in memory unit 313 in advance. These evaluation patterns may be determined by learning.

FIGS. 7 to 11 are each a cross-sectional view illustrating one variant configuration of the earphone.

Figure 7:
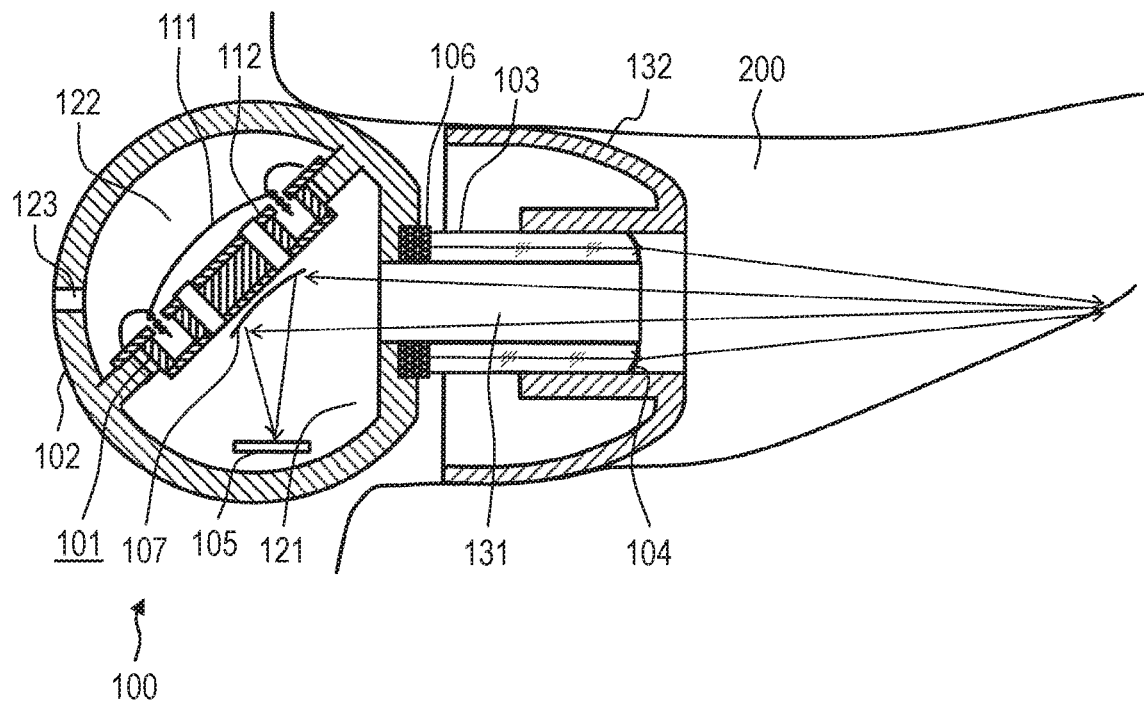
FIG. 7 is a cross-sectional view illustrating one variant configuration of the earphone.

With reference to FIG. 7, audio transmitter 101 may be tilted relative to sound passage 131. Diaphragm 111 may be disposed in second chamber 122. Reflector 107 may be attached to magnetic circuit 112.

Figure 8:
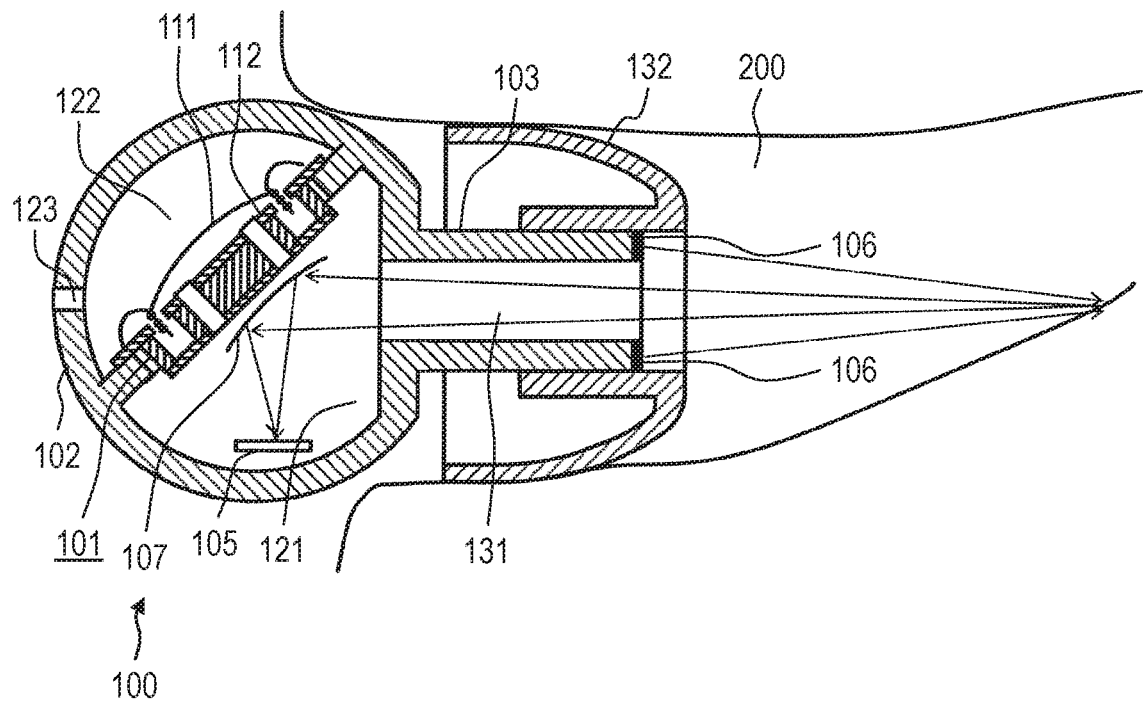
FIG. 8 is a cross-sectional view illustrating another variant configuration of the earphone.

With reference to FIG. 8, light emitter 106 may be disposed on the top end of sound passage pipe 103 adjacent to external auditory canal 200. In this case, light emitter 106 doubles as a radiator for radiating light into external auditory canal 200. Preferably, light emitter 106 should be an element that emits planar light. Examples of the light emitter include organic light-emitting diodes.

Figure 9:
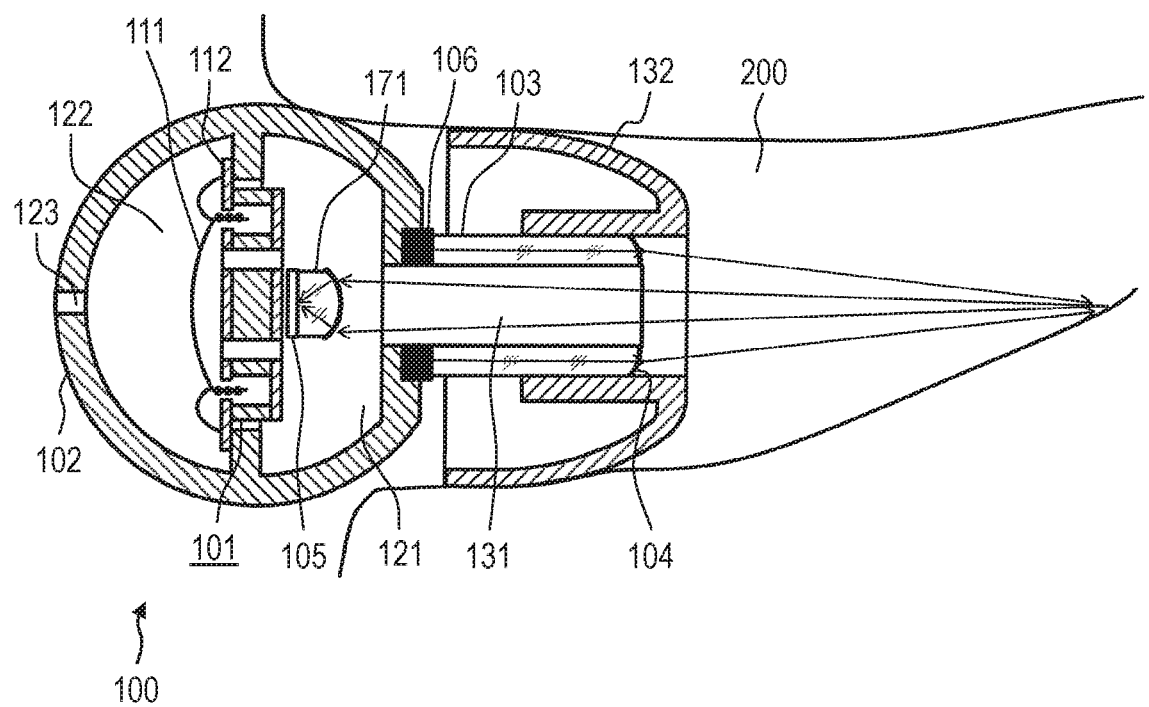
FIG. 9 is a cross-sectional view illustrating another variant configuration of the earphone.

With reference to FIG. 9, audio transmitter 101 may be disposed perpendicular to the axis of tubular sound passage pipe 103. Diaphragm 111 may be disposed in second chamber 122. Light receiver 105 may be mounted on magnetic circuit 112 such that light receiver 105 faces sound passage 131. Condenser 171 or any other lens may be disposed between light receiver 105 and sound passage pipe 103 to concentrate light that has passed through sound passage 131 onto light receiver 105. This configuration allows reflected light that has passed through sound passage 131 to be directly projected on light receiver 105. This in turn enables accurate detection of a change in the state of external auditory canal 200 even if the quantity of light passing through sound passage 131 is small.

Figure 10:
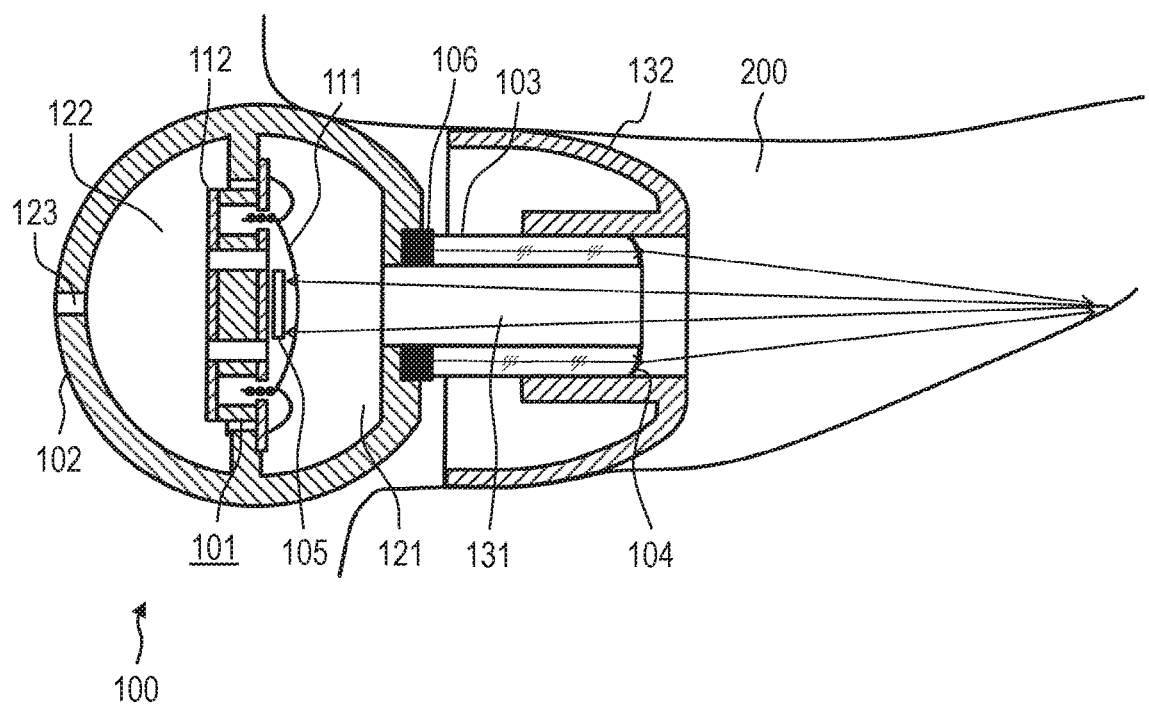
FIG. 10 is a cross-sectional view illustrating another variant configuration of the earphone.

With reference to FIG. 10, diaphragm 111 of audio transmitter 101 disposed perpendicular to the axis of tubular sound passage pipe 103 may be formed from a transparent material that allows reflected light passing through sound passage 131 to pass through. Diaphragm 111 may be disposed in first chamber 121. Light receiver 105 may be mounted on magnetic circuit 112 such that light receiver 105 is disposed between magnetic circuit 112 and diaphragm 111.

Figure 11:
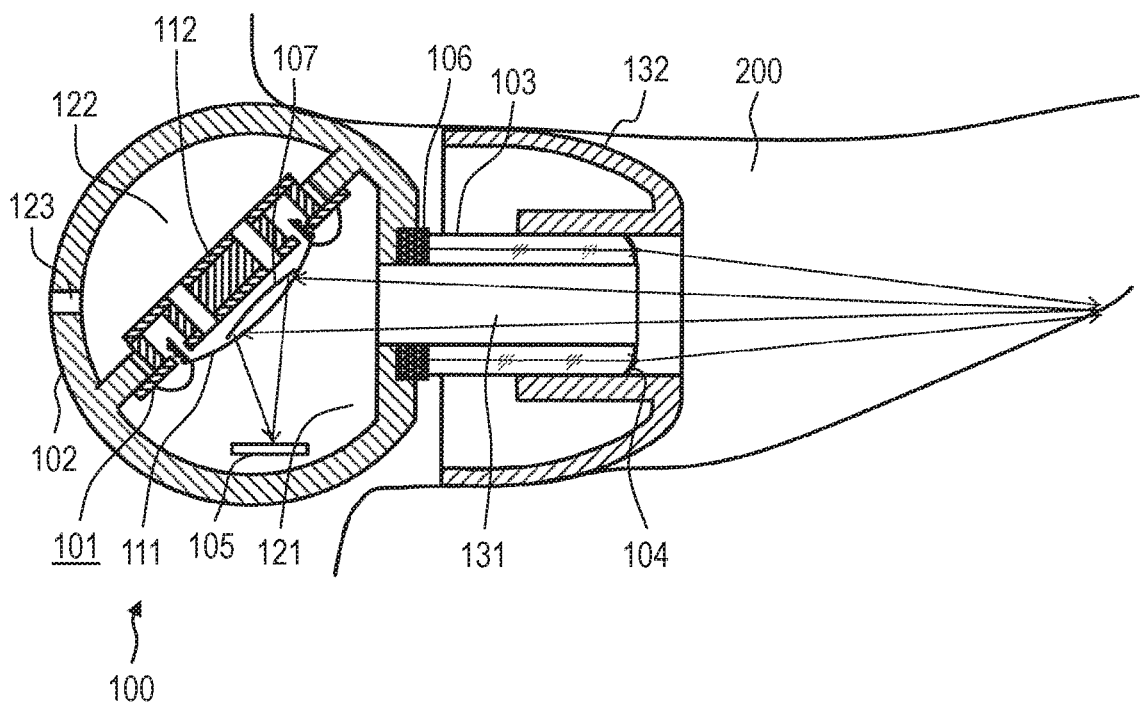
FIG. 11 is a cross-sectional view illustrating another variant configuration of the earphone.

With reference to FIG. 11, diaphragm 111 of audio transmitter 101 tilted relative to the axis of tubular sound passage pipe 103 may be a transparent component that allows reflected light passing through sound passage 131 to pass through. Diaphragm 111 may be disposed in first chamber 121. Reflector 107 may be mounted on magnetic circuit 112 such that reflector 107 is disposed between magnetic circuit 112 and diaphragm 111.

In earphone 100 illustrated in FIGS. 10 and 11, diaphragm 111 is a transparent component, and light receiver 105 or reflector 107 is disposed between magnetic circuit 112 and diaphragm 111. Thus, earphone 100 has no obstacle to the transmission of sound at least between diaphragm 111 and sound passage 131. This configuration enables light receiver 105 to efficiently receive light that has passed through sound passage 131 while ensuring sound quality required for earphone 100. This in turn enables light receiver 105 to transmit signals having a high signal-to-noise (S/N) ratio for use in generating signals for controlling an external device.

Figure 12:
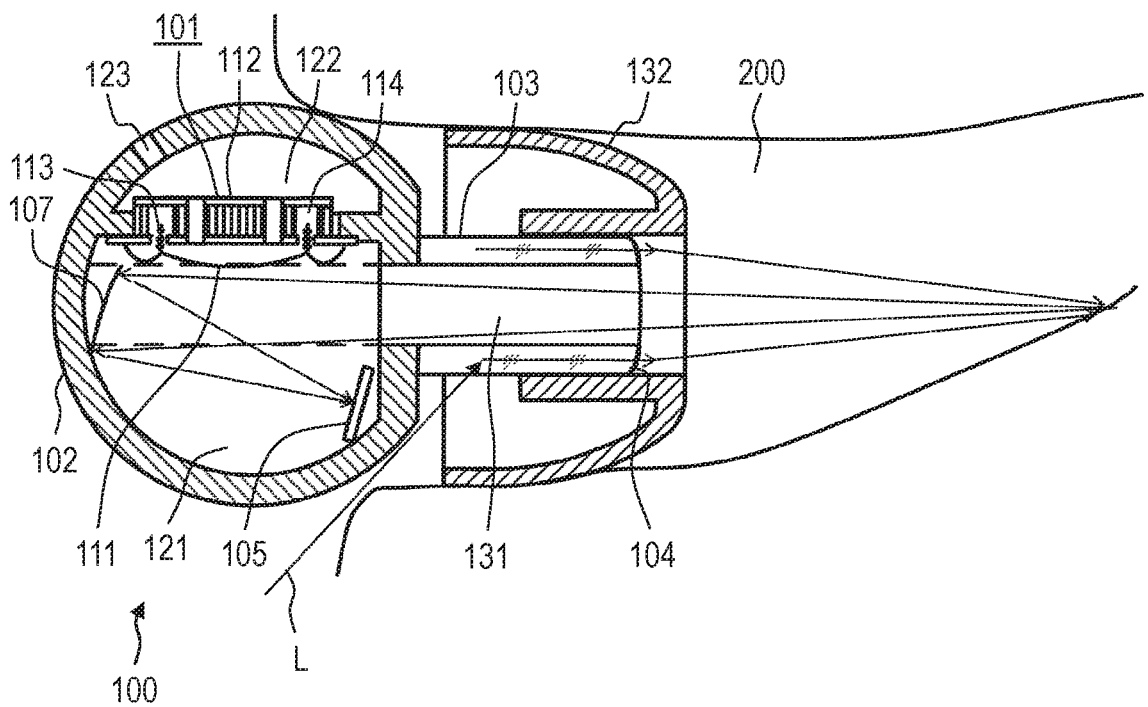
FIG. 12 is a cross-sectional view illustrating another variant configuration of the earphone.

With reference to FIG. 12, earphone 100 may have no light emitter 106 and may let radiator 104 radiate light by utilizing light L incident on sound passage pipe 103 through a gap that exists between external auditory canal 200 and earphone 100 while earphone 100 is put on an ear.

Ear pad 132 may be made up of a transparent or translucent component, and the earphone may use light incident on ear pad 132 instead of radiating light from radiator 104.

Earphone 100 according to any of the exemplary embodiments described above may be provided with an opening between housing 102 and sound passage pipe 103 to adjust sound quality.

If radiator 104 according to any of the exemplary embodiments described above has a lens with a pebble-grained surface or a planar light-emitting element, such as an organic light-emitting diode, that acts as a light emitter, radiator 104 radiates diffused light into external auditory canal 200. In this case, light comes into sound passage 131 in different directions. Thus it is preferable that inner surfaces of sound passage pipe 103 and first chamber 121 of housing 102 be each a reflecting surface.

An earphone according to the present disclosure doubles as an input device that controls an external device. For example, the earphone can control an external device such as a music player, a smartphone, or a tablet-type terminal while transmitting sound that is converted from audio signals sent from any of these devices.

What is claimed is:
1. An earphone comprising:
   an audio transmitter configured to transmit sound;
   a housing having an internal space for containing the audio transmitter;
   a sound passage pipe having a tubular shape and configured to be inserted into an external auditory canal to guide sound produced at the audio transmitter into the external auditory canal;
   a radiator configured to radiate light into the external auditory canal;
   a light receiver disposed in the internal space of the housing and configured to convert the light into a signal, the light having been reflected off the external auditory canal and passed through an internal space of the sound passage pipe; and
   a condenser in the internal space of the housing, the condenser concentrating the light that has passed through the internal space of the sound passage pipe,
   wherein the housing, the sound passage pipe, and the radiator are disposed in this order,
   the audio transmitter includes a first surface and a second surface opposite to each other, the light receiver is on the first surface, and
the audio transmitter includes a diaphragm on the second surface.

2. The earphone according to claim 1, wherein the condenser has a lens surface for concentrating the light.

3. The earphone according to claim 1, wherein the light receiver is between the audio transmitter and the condenser.

* * * * *